US00PP37065P2

(12) United States Plant Patent
van Geest

(10) Patent No.: US PP37,065 P2
(45) Date of Patent: Oct. 28, 2025

(54) ***FICUS* PLANT NAMED 'ESPE2006'**

(50) Latin Name: ***Ficus elastica* Roxb.**
Varietal Denomination: ESPE2006

(71) Applicant: J. Van Geest Holding B.V., 's Gravenzande (NL)

(72) Inventor: Jan van Geest, 's Gravenzande (NL)

(73) Assignee: J. VAN GEEST HOLDING B.V., 's Gravenzande (NL)

( * ) Notice: Subject to any disclaimer, the term of this patent is extended or adjusted under 35 U.S.C. 154(b) by 0 days.

(21) Appl. No.: 18/831,404

(22) Filed: Jan. 14, 2025

(51) Int. Cl.
*A01H 6/00* (2018.01)
*A01H 5/12* (2018.01)

(52) U.S. Cl.
USPC ..... Plt./211

(58) Field of Classification Search
USPC ..... Plt./211
CPC ..... A01H 6/00; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct variety of *Ficus elastica* plant named 'ESPE2006' which is characterized by the combination of a compact growth habit, glossy ovate foliage that is held upright and outward on the unbranched main stems, foliage with a very dark green general coloration on the upper surface and light red on the lower surface, main foliar veins that generally appear red on both the upper and lower surfaces, and the stability of all characteristics from generation to generation.

3 Drawing Sheets

Latin name of the genus and species: The Latin name of the genus and species of the novel variety disclosed herein is *Ficus elastica* Roxb.

Variety denomination: The inventive variety of *Ficus* disclosed herein has been given the variety denomination 'ESPE2006'.

BACKGROUND OF THE INVENTION

Parentage: 'ESPE2006' originated as a naturally occurring, whole-plant mutation of a *Ficus elastica* 'ESPETINEKE' plant (not patented). The inventor discovered the mutation in the summer of 2015 at a commercial greenhouse located in 's-Gravenzande, The Netherlands, growing amongst a cultivated population of 'ESPETINEKE' plants. The candidate variety was ultimately selected for its dense dark green glossy foliage with red petiole and midrib that grows in a whorl with a carinate aspect from the main stem.

Asexual Reproduction: Asexual reproduction of 'ESPE2006', by way of stem cuttings, was first initiated in September of 2015 at a commercial greenhouse in 's-Gravenzande, the Netherlands. Through ten subsequent generations, the unique features of this cultivar have proven to be stable and true to type.

SUMMARY OF THE INVENTION

The cultivar 'ESPE2006' has not been observed under all possible environmental conditions and the phenotype may vary somewhat with variations in environment such as temperature, water availability, and light intensity, without, however, any variance in genotype. The following traits have been repeatedly observed and are determined to be the unique characteristics of 'ESPE2006'. These characteristics in combination distinguish 'ESPE2006' as a new and distinct *Ficus* cultivar:

1. *Ficus* 'ESPE2006' exhibits a compact growth habit with an unbranched main stem bearing glossy, broadly ovate foliage with an upward attitude; and
2. *Ficus* 'ESPE2006' exhibits foliage that is slightly to moderately carinate and slightly concave; and
3. *Ficus* 'ESPE2006' exhibits juvenile foliage that is colored dark grey-brown with strong dark yellow-green suffusion, adaxially, and greyed-orange, with yellow-green and greyed-green irregular marbling, and red suffusion on the abaxial surface; and
4. *Ficus* 'ESPE2006' exhibits mature foliage that is colored dark greyed-green with strong dark greyed-purple suffusion on the adaxial surface, and a mixture of grey-brown and brown, with yellow-green irregular marbling, on the abaxial surface; and
5. *Ficus* 'ESPE2006' exhibits juvenile foliage with red main veins, adaxially, and grey-brown with strong red suffusion, abaxially; and
6. *Ficus* 'ESPE2006' exhibits mature foliage with yellow-green main veins with red flecking and striation, adaxially, and grey-brown with strong red suffusion, abaxially.

BOTANICAL DESCRIPTION OF THE PLANT

Figure 1:
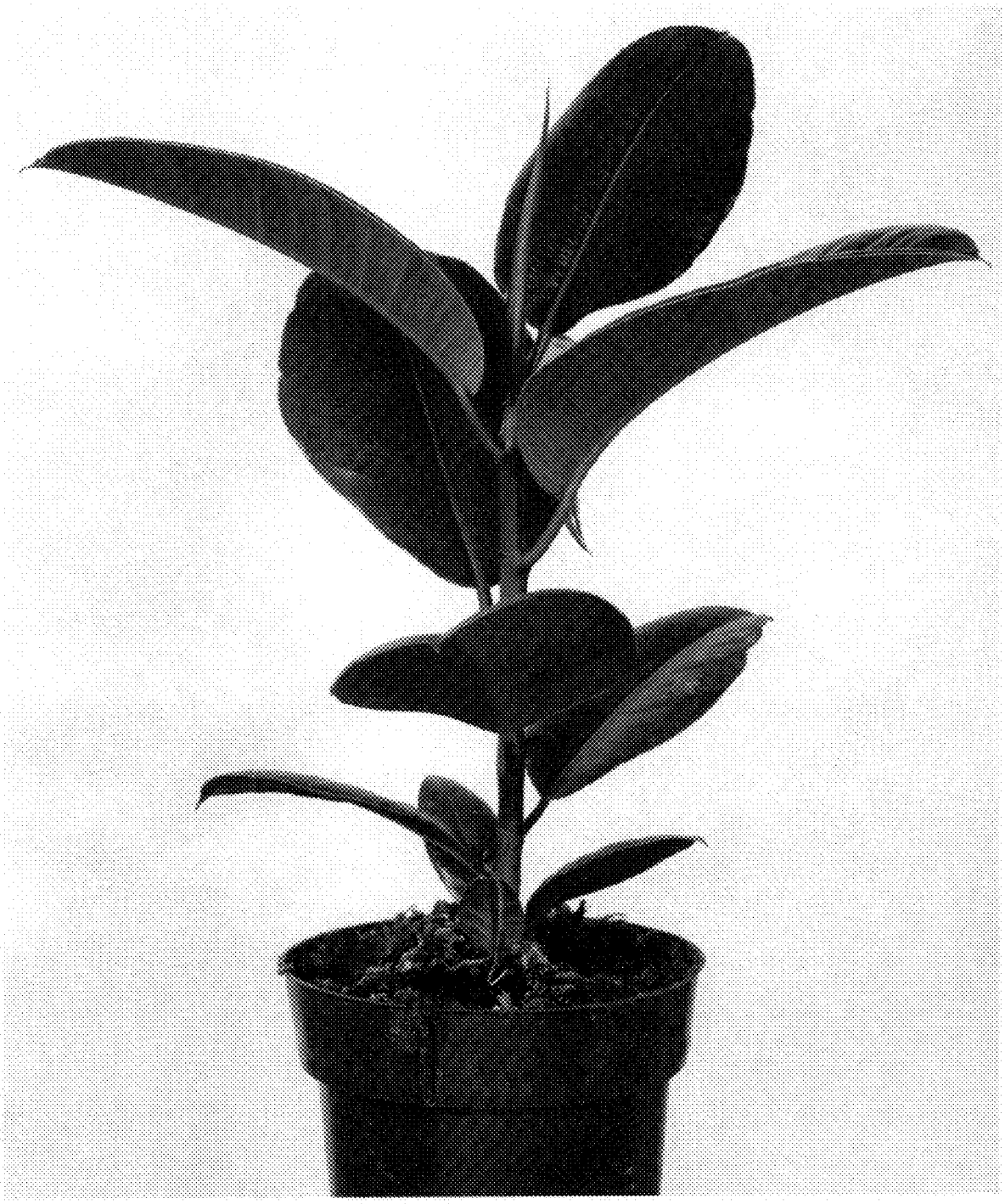
FIG. 1 illustrates, as nearly true as it is reasonably possible to make the same in color photographs of this type, an exemplary plant of 'ESPE2006' grown in a commercial greenhouse in 's-Gravenzande, the Netherlands. This plant is approximately 12 months old, shown planted in a 15 cm container.
Figure 2:
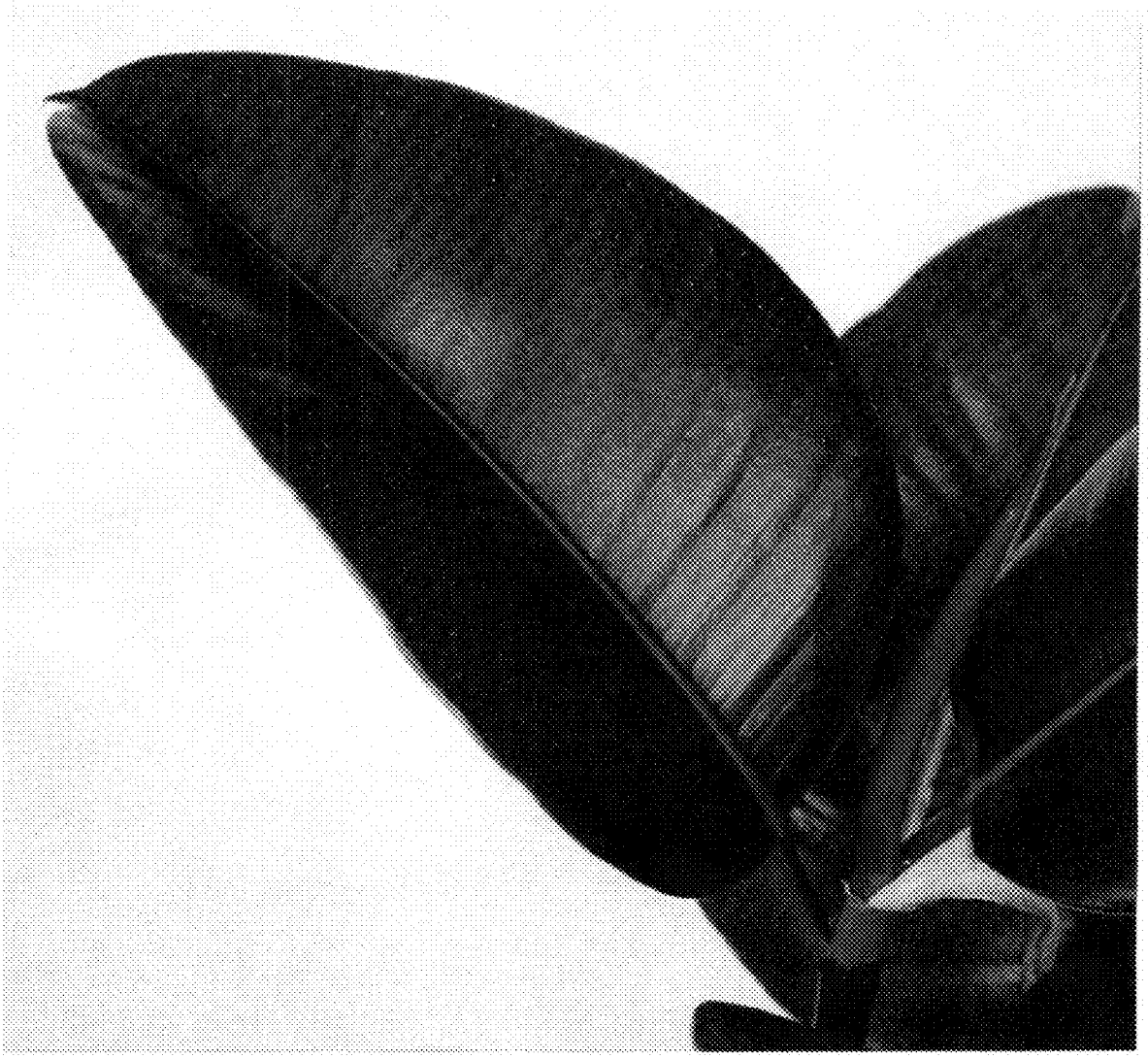
FIG. 2 illustrates, as nearly true as it is reasonably possible to make the same in color photographs of this type, the mature foliage on the adaxial side of 'ESPE2006'.
Figure 3:
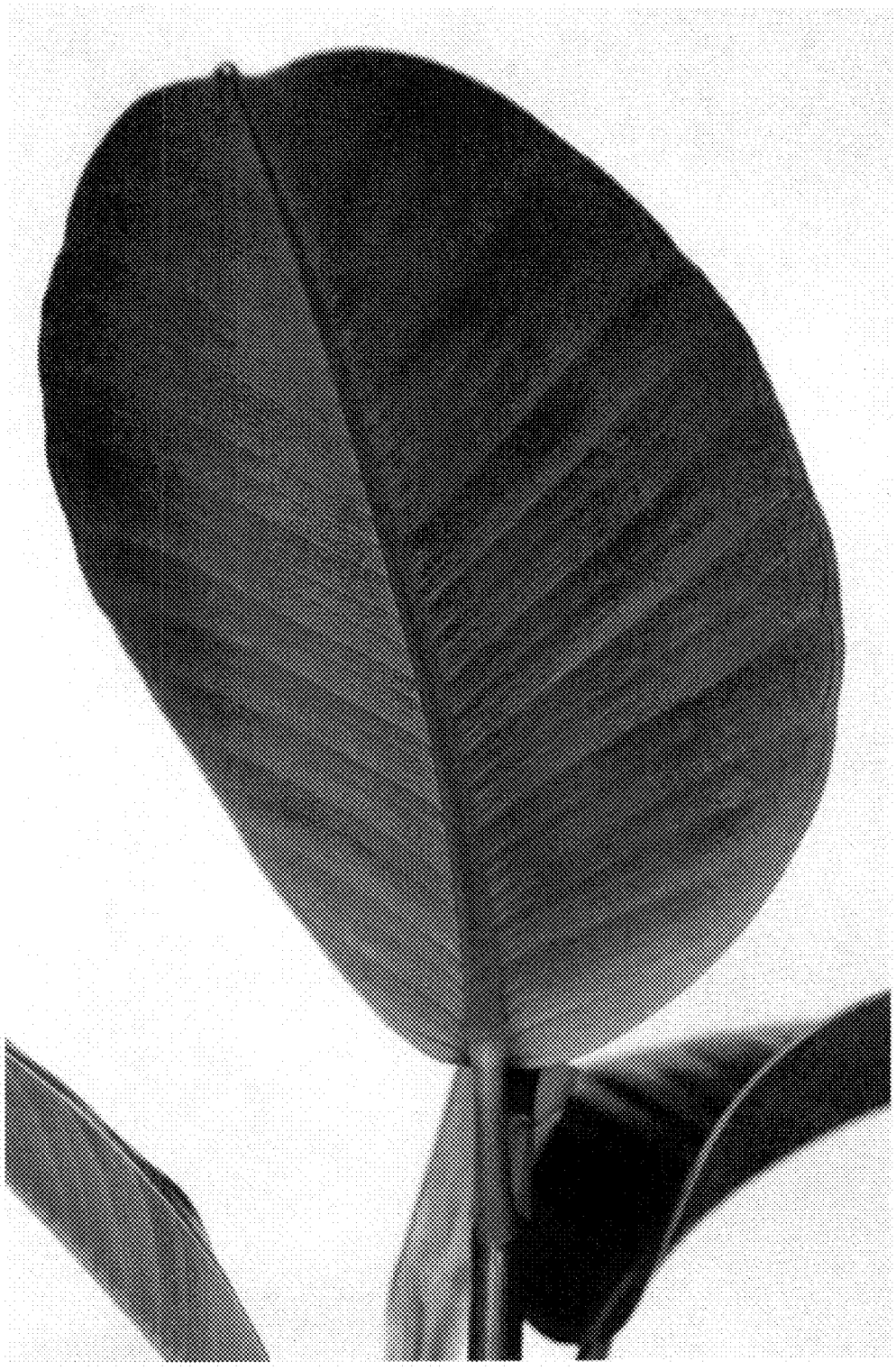
FIG. 3 illustrates, as nearly true as it is reasonably possible to make the same in color photographs of this type, the mature foliage on the abaxial side of 'ESPE2006'.

The following observations and measurements were made in April of 2024 and describe a sample set of six 12 month-old 'ESPE2006' plants grown in 15 cm nursery pots, at a greenhouse in 's-Gravenzande, the Netherlands. Plants were produced in a greenhouse with full sun exposure, ebb and flood irrigation tables, no supplemental fertilizer, and no preventative or pest control measures utilized.

Those skilled in the art will appreciate that certain characteristics of 'ESPE2006' will vary with the age of the plant. 'ESPE2006' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'ESPE2006' and comparisons with the parent plant and most similar variety known to the inventor are provided below.

Plant description:

*Growth habit*.—Upright evergreen perennial.

*Plant form*.—Obovate to broad oblong.

*Average height*.—36.2 cm from the soil level to the top of the foliar plane.

*Plant spread*.—Average of 35.9 cm.

*Plant vigor*.—Moderately vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 18 weeks to produce a marketable finished plant in a 17 cm pot.

*Disease and pest resistance*.—Neither resistance nor susceptibility to typical *Ficus elastica* pests and diseases has been observed.

*Environmental tolerances*.—Adapt to, at least, USDA Zones 10 through 13 and temperatures as high as 40 degrees Celsius; moderate tolerance to rain; low to moderate tolerance to wind.

Root system:

*General*.—Moderately dense, moderately branched rooting; roots are slightly fibrous.

*Distribution in the soil profile*.—Moderately deep.

*Diameter of roots*.—1.5 mm on average.

*Texture*.—Smooth; glabrous.

*Color*.—Greyed-yellow, nearest to RHS 162D.

Stems and branches:

*General branching habit*.—A single, unbranched main stem.

*Main stem*.—Quantity — One. Length — Approximately 24.0 cm. Diameter — Approximately 1.1 cm. Internode length — Approximately 3.6 cm. Attitude — Near vertical. Aspect — Rounded. Strength — Strong. Texture — Glabrous, with lenticels. Luster — Slightly glossy. Color, juvenile — Yellow-green, nearest to RHS 152A. Color, mature — Yellow-green, nearest to RHS 146A Color at the leaf nodes — At every node there is a thin radial ring around the stem which is approximately 0.4 mm wide and colored greyed-orange, nearest to in between RHS 164B and 164C. Color of the oldest wood — Yellow-green, nearest to RHS 146A and striated with a greyed-orange coloration, nearest to a combination of RHS 164C and 164D.

*Lenticels*.—Length — 0.5 mm. Diameter — 0.5 mm. Color — Greyed-orange, nearest to RHS 164B.

Foliage:

*Arrangement*.—Alternate.

*Division*.—Simple.

*Quantity*.—10 leaves per main stem.

*Attitude*.—Upward, near a 45-degree angle.

*Lamina*.—Shape — Broad ovate. Aspect — Slightly to moderately carinate and slightly concave. Dimensions — 19.5 cm long and 13.3 cm wide. Apex — Broad abruptly acute. Base — Rounded. Margin — Entire; slightly revolute. Texture of the adaxial surface — Smooth; glabrous; sparsely covered with small circular glands at the marginal zone. Glands are 0.3 mm in diameter and colored yellow-green, nearest to RHS 150D. Texture of the abaxial surface — Smooth; glabrous. Luster of the adaxial surface — Moderately glossy. Luster of the abaxial surface — Moderately glossy. Color — Juvenile foliage, adaxial surface — Nearest to a combination of grey-brown and yellow-green, RHS N199B, and strongly suffused with yellow-green, nearest to RHS 146A; margins are irregularly and very lightly marbled red, nearest RHS 39B. Juvenile foliage, abaxial surface — Greyed-orange, nearest to a mixture of RHS 174A and 177B, with yellow-green and greyed-green irregular marbling, nearest to a combination of RHS 147A and 189A; suffused with red, nearest to RHS 39B. Mature foliage, adaxial surface — Greyed-green, nearest to in between RHS 189A and N189A, and strongly suffused with greyed-purple, nearest to RHS N186A. The marginal zones are lightly and irregularly marbled with a combination of red and greyed-orange, nearest to RHS 37A and a blend of 37C and 174D. Mature foliage, abaxial surface — Nearest to a mixture of grey-brown and brown, RHS N199B and 200D, with yellow-green irregular marbling, nearest to RHS 146A; suffused with red, nearest to RHS 39B. Venation — Pattern — Pinnately reticulate. Color, adaxial surface — Juvenile veins are red, nearest to a combination of RHS 48C and 48D. Mature veins are yellow-green, nearest to RHS 147A, and strongly flecked and striated with red, nearest to a combination of RHS 48C and 48D. Color, abaxial surface — Grey-brown, nearest to RHS 199B and 200D, and strongly suffused with red, nearest to RHS 48C. Petiole — Cross-section — Terete. Diameter — 0.5 cm tall and 0.55 cm wide. Strength — Strong. Texture — Smooth; glabrous. Luster — Moderately glossy. Color, adaxial surface — Juvenile petioles are yellow-green, RHS 152A, and strongly suffused with red, nearest to RHS 48C. Mature petioles are colored with a blend of yellow-green and grey-brown, RHS 152A and N199A. Color, abaxial surface — Juvenile petioles are yellow-green, RHS 152A, and strongly suffused with red, nearest to RHS 48C. Mature petioles are yellow-green, nearest to RHS 152A. Stipule — General — A single stipule is present at the base of each leaf on the main stem; the stipule envelops the juvenile leaves prior to unfurling and later senesces once the leaf is fully open. Shape — Lanceolate. Length — 14.5 cm. Width — 2.6 cm. Cross-section — Concave. Apex — Acuminate. Base — Broad cuneate. Margin — Entire. Texture, adaxial — Smooth; glabrous. Texture, abaxial — Smooth; glabrous. Luster — Matte on both the adaxial and abaxial surfaces. Color, adaxial surface — Red, nearest to a combination of RHS 49A and 49B. Color, abaxial surface — Red, nearest to RHS 48A.

Inflorescence: No flowering has been observed to date.

COMPARISON WITH THE PARENT PLANT

Plants of the new cultivar 'ESPE2006' differ from the parent, *Ficus elastica* 'ESPETINEKE' (not patented) in the following characteristics described in Table 1 below.

TABLE 1

| Characteristic | 'ESPE2006' | The parent |
|---|---|---|
| General coloration of the juvenile foliage, adaxial surface. | Grey-brown and strongly suffused with yellow-green, generally appearing as a darker shade of green; margins are irregularly and very lightly marbled red. | Dark yellow-green, suffused with greyed-brown, generally appearing as a lighter shade of green. |
| General coloration of the juvenile foliage, abaxial surface. | Greyed-orange with yellow-green and greyed-green irregular marbling. | Light yellow-green and suffused with greyed-yellow. |

TABLE 1-continued

| Characteristic | 'ESPE2006' | The parent |
|---|---|---|
| General coloration of the mature foliage. | Greyed-green and strongly suffused with greyed-purple; marginal zones are lightly and irregularly marbled with a combination of red and greyed-orange. | Much lighter than 'ESPE2006'. White yellow margins with light green variegation and a green midrib. |
| Internodal spacing. | Longer than the parent. | Shorter than 'ESPE2006' and with more frequency of leaves along the main stem. |

COMPARISON WITH THE CLOSEST KNOWN COMPARATOR

Plants of the new cultivar 'ESPE2006' are most similar to the cultivar, *Ficus elastica* 'Robusta' (not patented). A comparison of 'ESPE2006' with *Ficus* 'Robusta' is described in Table 2 below.

TABLE 2

| | 'ESPE2006' | 'Robusta' |
|---|---|---|
| Branching Habit. | Leaves of this variety are fewer due to its basal branching habit. | More leaves and branches than 'ESPE2006'. |
| Foliage coloration. | Darker green with more red-brown underneath, purple variegation and red midrib stand out as strong difference from 'Robusta'. | Green glossy leaves with a greyed-green underside. |

That which is claimed is:

1. A new and distinct variety of *Ficus elastica* plant named 'ESPE2006', substantially as described and illustrated herein.

* * * * *